(12) United States Patent
Takami et al.

(10) Patent No.: US 11,971,381 B2
(45) Date of Patent: Apr. 30, 2024

(54) GAS DETECTION DEVICE

(71) Applicant: Osaka Gas Co., Ltd., Osaka (JP)

(72) Inventors: Susumu Takami, Osaka (JP); Atsushi Nonaka, Osaka (JP); Hisao Onishi, Osaka (JP)

(73) Assignee: Osaka Gas Co., Ltd., Osaka (JP)

(*) Notice: Subject to any disclaimer, the term of this patent is extended or adjusted under 35 U.S.C. 154(b) by 524 days.

(21) Appl. No.: 17/272,967

(22) PCT Filed: Sep. 5, 2018

(86) PCT No.: PCT/JP2018/032826
§ 371 (c)(1),
(2) Date: Mar. 3, 2021

(87) PCT Pub. No.: WO2020/049643
PCT Pub. Date: Mar. 12, 2020

(65) Prior Publication Data
US 2021/0208092 A1 Jul. 8, 2021

(51) Int. Cl.
| | | |
|---|---|---|
| *G01N 27/14* | (2006.01) | |
| *G01N 27/406* | (2006.01) | |
| *G01N 27/407* | (2006.01) | |
| *G01N 33/00* | (2006.01) | |
| *G01N 27/22* | (2006.01) | |

(52) U.S. Cl.
CPC ......... *G01N 27/14* (2013.01); *G01N 27/4067* (2013.01); *G01N 27/4075* (2013.01); *G01N 33/0009* (2013.01); *G01N 2027/222* (2013.01)

(58) Field of Classification Search
USPC ............................................. 73/31.05, 31.06
See application file for complete search history.

(56) References Cited

U.S. PATENT DOCUMENTS

| | | | | |
|---|---|---|---|---|
| 2,125,743 A | * | 8/1938 | Sweeney | C01B 3/40 |
| | | | | 423/654 |
| 5,863,503 A | * | 1/1999 | Kudo | G01N 33/0037 |
| | | | | 436/118 |
| 5,886,638 A | * | 3/1999 | Tanguay | G08B 29/145 |
| | | | | 73/31.06 |

(Continued)

FOREIGN PATENT DOCUMENTS

| | | | |
|---|---|---|---|
| JP | 2000356615 A | | 12/2000 |
| JP | 2002333426 A | * | 11/2002 |

(Continued)

OTHER PUBLICATIONS

Office Action issued in TW107132362 dated Sep. 13, 2022.
Office Action issued in TW11120170820 dated Feb. 23, 2022.

*Primary Examiner* — Clayton E. LaBalle
*Assistant Examiner* — Warren K Fenwick
(74) *Attorney, Agent, or Firm* — The Webb Law Firm

(57) ABSTRACT

Provided is a gas detection device used in a humid environment such as a kitchen or a cooking room, which is excellent in moisture resistance and also excellent in sensitivity. In a gas detection device which includes a thin film type gas sensor including a heater portion, a gas detection portion, and a catalyst portion on a substrate, energizes the heater portion to heat the gas detection portion and the catalyst portion, and detects the detection target gas, the gas sensor configured by supporting a catalyst metal containing platinum as a main component on a support containing a transition metal oxide as a main component is adopted.

10 Claims, 7 Drawing Sheets

(56) References Cited

U.S. PATENT DOCUMENTS

| | | | | |
|---|---|---|---|---|
| 8,003,055 B1 * | 8/2011 | Muradov | ............... | G01N 31/22 |
| | | | | 73/23.31 |
| 8,043,567 B2 * | 10/2011 | Sasaki | ................. | H01M 8/0447 |
| | | | | 422/94 |
| 8,117,894 B2 * | 2/2012 | Abdullah | ............. | G01N 27/122 |
| | | | | 340/634 |
| 8,567,231 B2 * | 10/2013 | Isomura | ............. | G01N 27/4067 |
| | | | | 73/23.31 |
| 8,578,758 B2 * | 11/2013 | Ito | ........................ | G01N 27/127 |
| | | | | 73/31.06 |
| 8,739,604 B2 * | 6/2014 | Krishna | ............. | G01N 27/4162 |
| | | | | 422/50 |
| 2010/0122568 A1 * | 5/2010 | Inoue | ................ | G01N 27/4065 |
| | | | | 73/31.05 |
| 2011/0126612 A1 * | 6/2011 | Shimizu | ................ | G01N 27/12 |
| | | | | 73/31.05 |

FOREIGN PATENT DOCUMENTS

| | | | | |
|---|---|---|---|---|
| JP | 200583840 A | | 3/2005 | |
| JP | 200724508 A | | 2/2007 | |
| JP | 200724509 A | | 2/2007 | |
| JP | 2007271441 A | * | 10/2007 | |
| JP | 2009103541 A | | 5/2009 | |
| JP | 2013190232 A | | 9/2013 | |
| JP | 2018048912 A | * | 3/2018 | ............ G01C 19/68 |
| JP | 201854592 A | | 4/2018 | |
| JP | 201854593 A | | 4/2018 | |
| JP | 2018054593 A | * | 4/2018 | |
| TW | 201627662 A | | 8/2016 | |
| TW | 201830008 A | | 8/2018 | |

\* cited by examiner

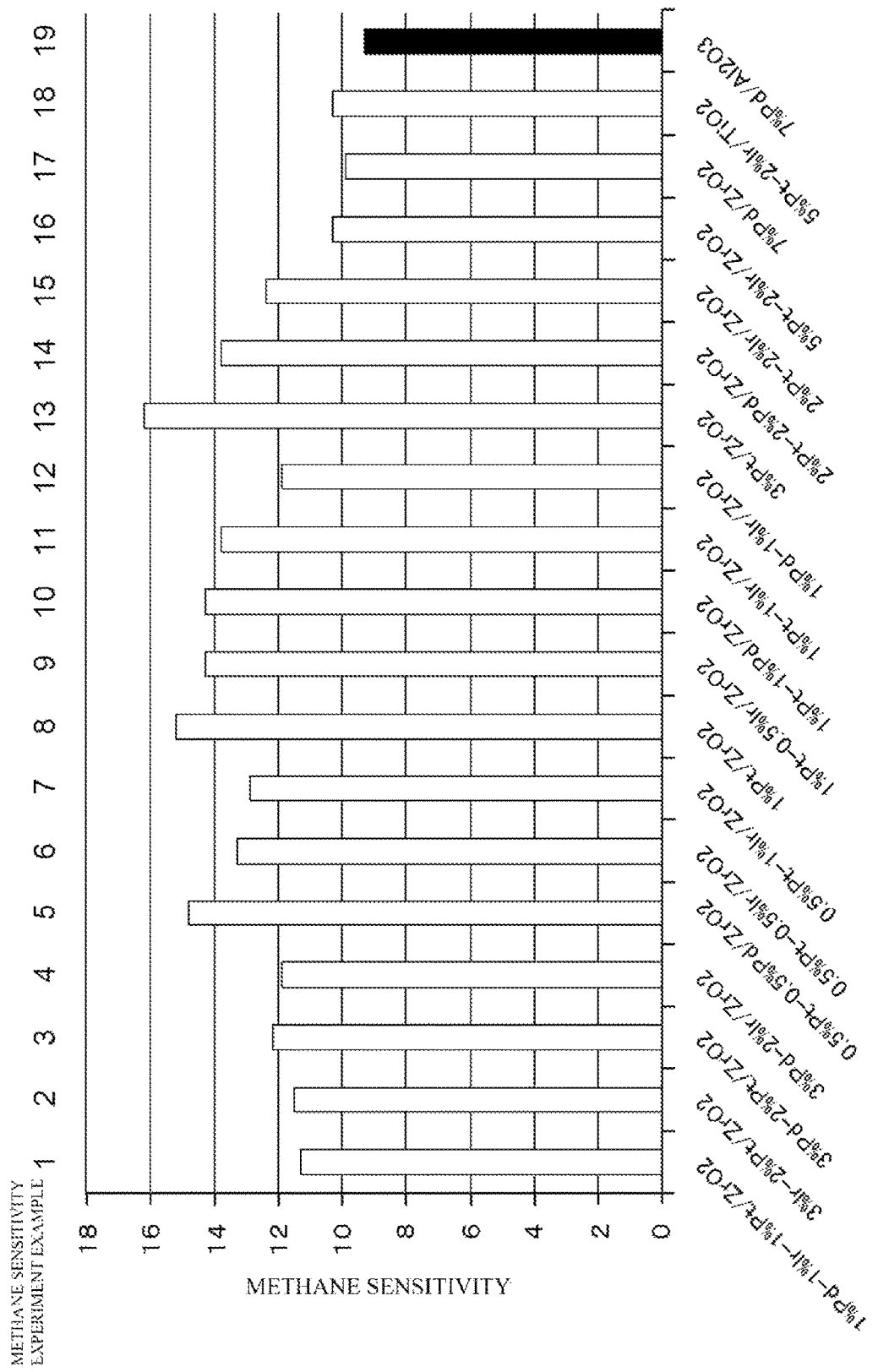

GAS DETECTION DEVICE

CROSS-REFERENCE TO RELATED APPLICATION

This application is the United States national phase of International Application No. PCT/JP2018/032826 filed Sep. 5, 2018, the disclosure of which is hereby incorporated by reference in its entirety.

BACKGROUND OF THE INVENTION

Field of the Invention

The present invention relates to a gas detection device which includes a gas sensor including a heater portion, a gas detection portion whose characteristics change due to contact with a detection target gas, and a catalyst portion provided to cover at least a part of the gas detection portion, energizes the heater portion to heat the gas detection portion and the catalyst portion, and detects the detection target gas.

Description of Related Art

Such a gas detection device is disclosed in JP-A-2013-190232 and JP-A-2007-24509.

Hereinafter, the gas detection devices described in these literatures will be described as an example.

The gas detection device is configured to include a gas sensor, a heating control unit for heating and driving the gas sensor, and a gas detection unit for detecting a change in the characteristics of a gas detection portion, in which heating by a heater portion is controlled by the heating control unit to heat the gas detection portion and a catalyst portion provided on the surface side thereof to appropriate temperatures depending on the kind of a detection target gas, and gas detection is performed.

The detection target gas includes flammable gas such as methane ($CH_4$) and propane ($C_3H_8$), and reducing gas such as carbon monoxide (CO) and hydrogen ($H_2$).

At the time of gas detection, the heating control unit applies pulse energization to the heater portion to heat the gas detection portion and the catalyst portion. In FIGS. 4(a), 4(b), and 4(c) of the present specification, this heating form is shown by a heating drive signal. FIGS. 4(a) and 4(b) are diagrams showing heating drive signals in a case where the detection target gas is a flammable gas, and FIG. 4(c) shows a case where the detection target gas is a flammable gas and a reducing gas.

As can be seen from FIG. 4(a), the energization of the heater portion includes a gas detection step Ts of performing energization and a heating suspension step Tr performed subsequent to the gas detection step Ts, and gas detection is repeated in a predetermined gas detection cycle Rt.

The detection of the detection target gas is generally performed immediately before the energization is stopped, as shown by the black dots in the figures.

When detecting the flammable gas, high temperature heating (High) is performed as shown in FIGS. 4(a) and 4(b), and miscellaneous gas which becomes an interfering gas at the time of detection is burned and removed at the catalyst portion.

Representative interfering gases include hydrogen ($H_2$), ethanol ($C_2H_5OH$), and carbon monoxide (CO), and the catalyst portion is also called an oxidation catalyst layer because of such functions. In the high temperature heating state, a flame-retardant flammable gas (representatively methane) that passes through the catalyst portion and reaches the gas detection portion can be detected.

A heating drive form shown in FIG. 4(c) is a form in which low temperature heating (Low) is performed subsequent to the high temperature heating (High), and a reducing gas (representatively carbon monoxide) is detected immediately before energization for the low temperature heating (Low) is stopped.

As shown in FIG. 4(a), while the gas detection step Ts is repeated in a predetermined gas detection cycle Rt, in the heating suspension step Tr between the gas detection steps Ts, the energization of the heater portion is stopped (off).

In a case where the gas sensor is a gas sensor that has a small heat capacity in a heated portion and enables pulse heating drive with high heating response, the energization in the gas detection step Ts is a form in which the energization time is about 0.05 seconds to 0.5 seconds, and the pulse energization is repeated in a gas detection cycle of about 20 seconds to 60 seconds with the heating suspension step Tr, whereby power-saving drive can be realized.

That is, in this example, the heating in the gas detection step Ts is pulse heating, and the pulse heating is repeated in a predetermined gas detection cycle Rt with the heating suspension step Tr in between.

In such a case, the heating suspension step Tr takes an overwhelmingly long time, and the gas sensor is only heated for an extremely short time.

In such a gas sensor, because of its low heat capacity and the like, the heating drive for gas detection may be so-called pulse heating, and a power-saving gas detection device that can use a battery as a power source is achieved.

JP-A-2013-190232 introduces a technique for performing preventive maintenance of a gas detection device, and JP-A-2007-24509 introduces a thin film gas sensor that suppresses moisture absorption by a gas sensing layer and maintains high sensitivity.

When the correspondence with the wording used in the background part introduced as above is shown in (the wording of JP-A-2013-190232 and the wording of JP-A-2007-24509), the gas detection portion is (a sensing layer 57, and a gas sensing layer 5), and the catalyst portion is (a selective combustion layer 58, and a gas selective combustion layer 5d).

As can be seen from the techniques disclosed in these patent literatures, in a gas sensor provided in this kind of gas detection device, as the catalyst portion, a sintered material in which palladium (Pd) or platinum (Pt) as a catalyst metal is supported on an alumina ($Al_2O_3$) support has been used.

Furthermore, in JP-A-2007-24509, aged deterioration of the gas sensor due to humidity is a problem to be solved, but it is proposed to adopt a moisture absorption suppression drive as shown in FIG. 1 of the same specification.

However, the inventors of the present invention investigated gas sensors of gas detection devices used in a humid environment such as a kitchen or a cooking room, and found that there are gas detection devices having a reduced methane sensitivity.

The technique disclosed in JP-A-2007-24509 proposes one measure that can be adopted in a case where the gas detection device is used in such a high humidity environment, but is not suitable for the purpose of obtaining a power-saving gas detection device because the moisture absorption suppression drive needs to be performed in the heating suspension step.

Furthermore, considering the sensor sensitivity to the detection target gas, while it is preferable that the sensitivity is as high as possible, it is determined according to the recent examination by the inventors that there is room for improvement in the gas sensor with an alumina support in the related art.

SUMMARY OF INVENTION

The present invention has been made in view of the above-mentioned problems, and an object thereof is to provide a gas detection device used in a humid environment such as a kitchen or a cooking room, which is excellent in moisture resistance and also excellent in sensitivity.

Furthermore, an object is to obtain a gas sensor that can be used in such a gas detection device.

A first characteristic configuration of the present invention is a gas detection device including: a gas sensor including a heater portion, a gas detection portion whose characteristics change due to a contact with a detection target gas, and a catalyst portion provided to cover at least a part of the gas detection portion, in which the gas detection device energizes the heater portion to heat the gas detection portion and the catalyst portion and detects the detection target gas, and the catalyst portion is configured by supporting a catalyst metal containing platinum as a main component on a support containing a transition metal oxide as a main component.

After diligent examinations, the inventors found that the main cause of a fluctuation in sensitivity over time in a gas detection device in the related art is the adsorption and accumulation of water onto alumina, which is the main component of a support of a catalyst portion. The alumina support has a strong interaction with water, so that the hydroxyl group (OH group) is adsorbed in the short term and the amount of chemisorbed water increases. Furthermore, water molecules (physisorbed water) that cannot be completely blown off during heating accumulate and the physisorbed water reacts with alumina to form hydrate, whereby the alumina is altered.

As a result, the function as a catalyst portion for burning the reducing gas and other interfering gases and the gas detection function are changed. In addition, due to the adsorption and accumulation of water, alumina is altered, the dispersed state of the catalyst metal such as palladium supported on the surface is deteriorated, and the surface area of the catalyst metal is reduced, so that the function as a catalyst portion is also deteriorated and is not recovered (irreversible change).

Furthermore, the temperature does not rise to the temperature required to detect the detection target gas. Due to these factors, it is presumed that the sensitivity to the above-mentioned detection target gas changes over time.

Such a finding that "the interaction between the support of the catalyst and water affects a change in sensitivity to methane over time" is not present in the findings in the related art, but is a completely new finding.

Based on these new findings, the inventors examined the material of the support of the catalyst portion and selected the transition metal oxide as the main component of the support.

In general, zirconium oxide, which is a representative example of the transition metal oxide, has not been actively used as the support of a catalyst portion because its specific surface area is smaller than that of alumina. The specific surface area of alumina is about 120 $m^2/g$, while the specific surface area of zirconium oxide is about 30 $m^2/g$, which is a difference of about 4 times. In the related art, the larger the surface area, the larger the area that interacts with the gas. Therefore, it has been considered that alumina has higher performance as the catalyst portion and zirconium oxide has lower performance when used as the support of a catalyst portion.

However, in opposition to this recognition in the related art, the inventors used zirconium oxide and titanium oxide instead of alumina as the support, conducted an experiment ([high humidity exposure experiment] described later) for investigating the effect of moisture in the air, and could confirm that the sensitivity of zirconium oxide and titanium oxide is less likely to fluctuate even in a high humidity compared to alumina. It was also confirmed that zirconium oxide and titanium oxide can suppress a decrease in sensitivity even in a high humidity environment compared to alumina. These are considered to be due to the small interaction between zirconium oxide and titanium oxide and water, and the effect is the same for transition metal oxides that also have a small interaction with water. Then, the present invention using the transition metal oxide as the support of the catalyst portion was completed.

Furthermore, regarding the sensor sensitivity, according to the present examination by the inventors, it was determined that even in a case where the same catalyst metal is adopted, the sensitivity is improved simply by changing the support of the catalyst portion from alumina to a transition metal oxide, and the sensitivity is further improved by optimizing the catalyst composition. In a case where zirconium oxide was used as the support, platinum as the catalyst metal showed high sensitivity.

Therefore, according to this configuration, as a gas detection device that detects gas using a gas sensor including a heater portion, a gas detection portion, and a catalyst portion, for example, regarding a gas detection device used in a humid environment such as a kitchen or a cooking room, a gas detection device that has excellent moisture resistance and can maintain high sensitivity could be obtained.

A gas sensor used in the gas detection device has the following configuration.

The gas sensor is configured to include a heater portion, a gas detection portion whose characteristics change due to contact with a detection target gas, and a catalyst portion covering at least a part of the gas detection portion, and the catalyst portion is obtained by supporting a catalyst metal containing platinum as a main component on a support containing a transition metal oxide as a main component.

Therefore, as described in a second characteristic configuration of the present invention, as the transition metal oxide as the main component of the support, one or both of zirconium oxide and titanium oxide can be adopted.

A third characteristic configuration of the present invention is that the catalyst portion is configured by supporting 0.3 mass % or more and 9 mass % or less of platinum as the catalyst metal on the transition metal oxide as the support.

According to this configuration, moisture resistance could be obtained by using the transition metal oxide as the support, and as will be described later in [Methane Sensitivity Experiment], by adopting platinum as the catalyst metal, a gas detection device having high sensitivity can be obtained compared to the case of using alumina as the support. Here, when the supported concentration of platinum is less than 0.3 mass %, a sufficient selective oxidizing ability cannot be obtained. When the supported concentration of platinum is higher than 9 mass %, the oxidizing ability becomes too high, and even methane is burned at the catalyst.

A fourth characteristic configuration of the present invention is that one or both of palladium and iridium are contained as the catalyst metal in addition to platinum as the main component.

According to this configuration, in combination with platinum, palladium and iridium could be mixed to obtain the same selective oxidizing property as a composite, and a gas detection device having good sensitivity could be obtained.

A fifth characteristic configuration of the present invention is that the detection target gas is detected by repeating a gas detection step of energizing the heater portion to heat the gas detection portion and the catalyst portion and detecting the detection target gas, and a non-detection step of setting temperatures of the gas detection portion and the catalyst portion to be in a state lower than temperatures of the gas detection portion and the catalyst portion in the gas detection step.

In this configuration, while the gas detection device repeats the gas detection step and the non-detection step, by setting the temperatures of the gas detection portion and the catalyst portion in the non-detection step to be in a state lower than the temperatures of both the portions in the gas detection step, for example, the gas detection portion and the catalyst portion can be managed to be at a temperature at which the effect of water can be reduced even if the temperature does not reach the temperature at which gas detection can be performed.

Such a non-detection step can be realized, for example, by combining heating suspension (stop of energization) and heating (energization) in any form. Here, if the temperatures of both the portions are managed so as not to be affected by water, which is the object of the present invention, the generation of hydrate newly found by the inventors can be effectively inhibited. Therefore, high sensitivity can be maintained for a long life while suppressing power consumption.

This operation is similar to the moisture absorption suppression drive described above. However, in the present invention, since the support forming the catalyst portion contains the transition metal oxide as the main component, the degree of heating or the frequency of heating can be reduced compared to the moisture absorption suppression drive disclosed in the same literature. As a result, a highly practical gas detection device can be realized.

A sixth characteristic configuration of the present invention is that the detection target gas is detected by repeating a gas detection step of energizing the heater portion to heat the gas detection portion and the catalyst portion and detecting the detection target gas, and a low heating step of performing energization to set temperatures of the gas detection portion and the catalyst portion to be temperatures lower than temperatures of the gas detection portion and the catalyst portion in the gas detection step.

By interposing the low heating step between the gas detection steps, the gas detection portion and the catalyst portion are in a heated state (for example, about 50° C.) higher than room temperature without being heated to a temperature at which gas detection can be performed. Therefore, a reduction in the effect of water on the catalyst portion, which is an object of the present invention, can be achieved.

Furthermore, by reducing the heating amount, the power consumption can be suppressed to a low level.

A seventh characteristic configuration of the present invention is that the detection target gas is detected by repeating a gas detection step of energizing the heater portion to heat the gas detection portion and the catalyst portion and detecting the detection target gas, and a heating suspension step of stopping the energization of the heater portion.

By adopting this configuration, gas detection can be performed with more saved power without heating the gas sensor at an unnecessary timing.

Here, it is understood that the effect of water on the catalyst portion is unlikely to occur in the gas detection step. This is because in this step, the gas detection portion and the catalyst portion are sufficiently heated, and it can be understood that water rarely adheres to the catalyst portion.

Contrary to this, in the heating suspension step, the energization of the heater portion is stopped, and the temperature of each portion rapidly drops to room temperature. Therefore, for example, in a gas detection device that periodically detects gas by performing pulse heating, the gas sensor is usually placed in an environment that is greatly affected by water (particularly in a warm and humid environment) only by being heated in a moment. As a result, it is considered that the problems described above are likely to occur over time. This can also be acknowledged from the fact that the step of performing the adsorption suppression drive in JP-A-2007-24509 introduced above is the heating suspension step of the present invention.

However, in the present invention, by using the transition metal oxide as the main component of the support of the catalyst portion and platinum as the main component of the catalyst metal, gas detection can be performed with high sensitivity without being affected by water.

An eighth characteristic configuration of the present invention is that a heating time in the gas detection step is shorter than a heating stop time in the heating suspension step.

By adopting this configuration, the heating time is short, and gas detection can be performed with high sensitivity while suppressing power consumption.

A ninth characteristic configuration of the present invention is that at least the heating in the gas detection step is pulse heating having a heating time of 0.05 seconds to 0.5 seconds, and at least a basic heating form of repeating the pulse heating in a gas detection cycle of 20 seconds to 60 seconds with the heating suspension step is performed.

The basic heating form refers to a heating method in normal times except for cases where the above heating conditions are not met regularly or irregularly for the purpose of measures against detection delay, suppression of false alarms, failure diagnosis, and performance improvement.

With this configuration, gas detection can be performed with further reduced power consumption.

In the configuration of the present invention, for example, even in the case of battery-powered methane detection, gas detection can be performed satisfactorily over a predetermined period required for the gas detection device.

A tenth characteristic configuration of the present invention is that a high temperature heating step of heating the gas detection portion and the catalyst portion to a temperature for detecting methane when detecting the detection target gas is further included.

According to this configuration, methane, which is very important for detecting city gas (natural gas) leakage as a kind of detection target gas, can be detected with high moisture resistance and high sensitivity.

BRIEF DESCRIPTION OF DRAWINGS

FIG. 3 is a comparison diagram showing the sensitivity of a gas detection device using various catalyst metals.

DESCRIPTION OF THE INVENTION

Figure 1:
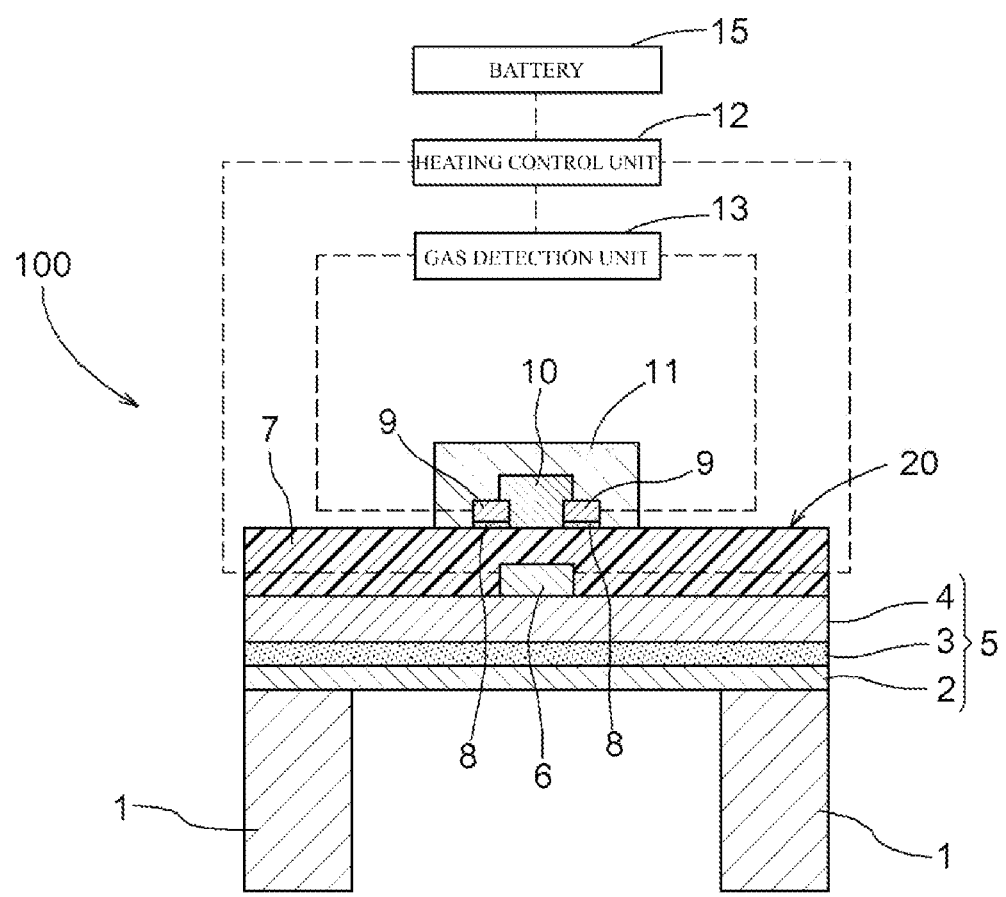
FIG. 1 is a diagram showing an outline of a gas detection device.

A gas detection device 100 according to the present embodiment will be described with reference to FIG. 1.

The gas detection device 100 is configured to include a sensor element 20 (an example of a gas sensor), a heating control unit 12, and a gas detection unit 13.

The gas detection device 100 has a battery 15 attached thereto and detects a detection target gas by obtaining power from the battery 15.

The sensor element 20 is a so-called power-saving gas sensor having a diaphragm structure. As is clear from FIG. 1, the sensor element 20 is configured to include a heater layer 6 (an example of a heater portion), a gas detection layer 10 (an example of a gas detection portion), and a catalyst layer 11 (an example of a catalyst portion) on a support layer 5 having a diaphragm structure. Therefore, the structure is such that the catalyst layer 11 is exposed to a surrounding environment, and the detection target gas passes through the catalyst layer 11 and reaches the gas detection layer 10. The reaching detection target gas comes into contact with the layer 10 and changes the characteristics of the layer 10. Here, specific examples of the characteristics include a resistance value or a voltage value.

The gas detection device 100 energizing the heater layer 6 by the heating control unit 12 to heat the gas detection layer 10 to an appropriate temperature for the kind of the detection target gas, and in a state where the temperature is held, detects the detection target gas based on a change in the characteristics of the gas detection layer 10.

Figure 4A:
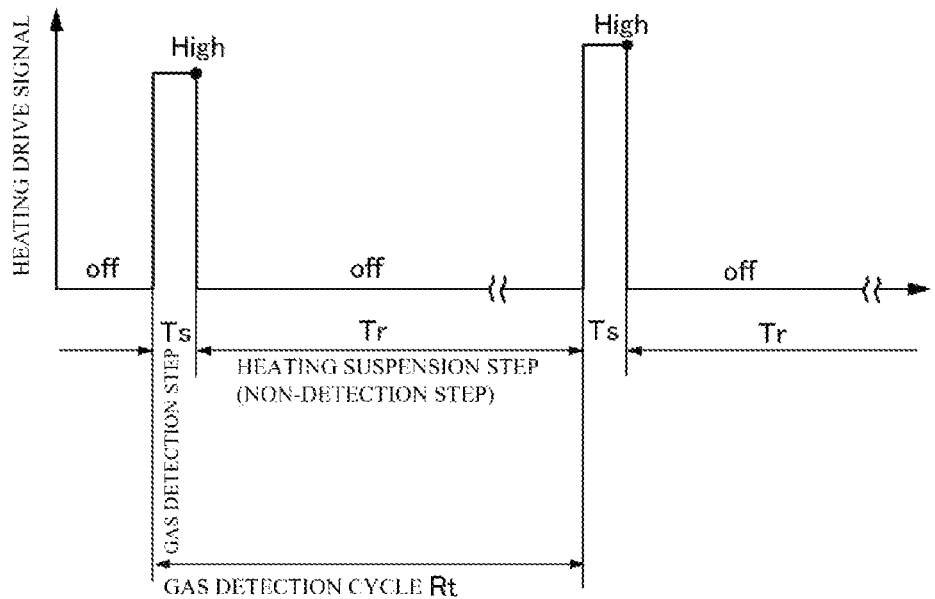
FIGS. 4(a)-4(c) are explanatory diagrams showing forms of heating drive.
Figure 4B:
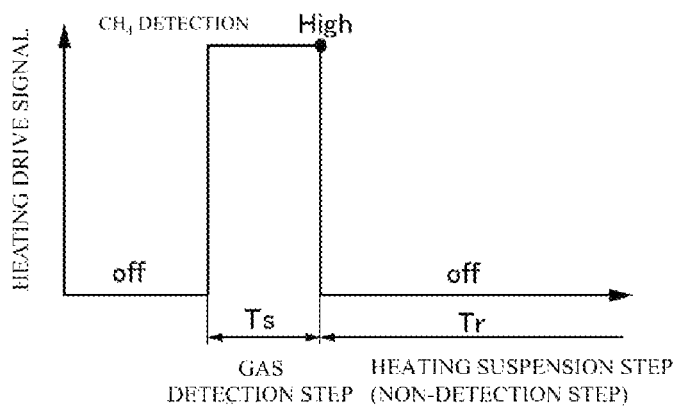
Figure 4C:
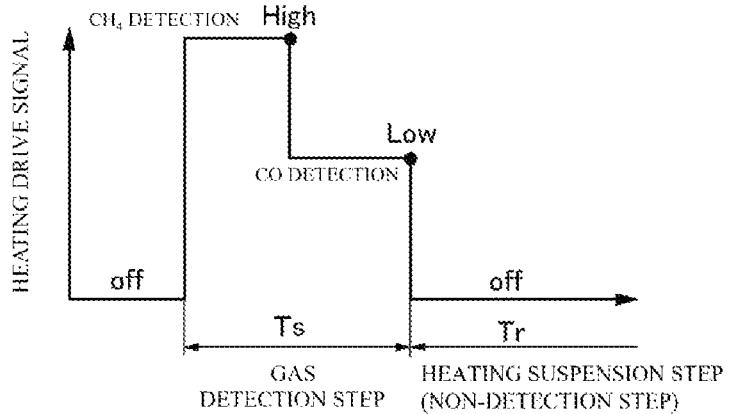

When detecting methane, the catalyst layer 11 is heated to a high temperature of 300° C. or higher by the heater layer 6 (High shown in FIGS. 4(a), 4(b), and 4(c)) to burn a reducing gas such as carbon monoxide and hydrogen and other interfering gases and allows methane having low activity to penetrate and diffuse through the catalyst layer 11 to reach the gas detection layer 10. Accordingly, the detection accuracy of methane is improved.

When detecting carbon monoxide, low temperature heating to 50° C. to 250° C. (Low shown in FIG. 4(c)) is performed by the heater layer 6 to burn a reducing gas such as hydrogen and other miscellaneous gases. Although a portion of carbon monoxide is burned, most of the carbon monoxide can penetrate and diffuse through the catalyst layer 11 to reach the gas detection layer 10. In this low temperature region, methane and the like having low activity are not detected by the gas detection layer 10.

In other words, the catalyst layer 11 heats an interfering gas (non-detection target gas) such as hydrogen gas and alcohol gas other than the detection target gas to an appropriate temperature to be burned so as not to reach the gas detection layer 10, and thus has a function of allowing the gas detection device 100 to have gas selectivity. Furthermore, the catalyst layer 11 also plays a role of improving the sensitivity by supplying oxygen to the surface of the gas detection layer 10.

(Sensor Element)

The sensor element 20 has a diaphragm structure in which an end portion of the support layer 5 is supported by a silicon substrate 1. The support layer 5 is formed by laminating a thermal oxidation film 2, a silicon nitride ($Si_3N_4$) film 3, and a silicon oxide ($SiO_2$) film 4 in this order. Then, the heater layer 6 is formed on the support layer 5, an insulating layer 7 is formed over the entire heater layer 6, a pair of bonding layers 8 are formed on the insulating layer 7, and an electrode layer (an example of an electrode) 9 is formed on the bonding layer 8. The heater layer 6 generates heat by being energized to heat the gas detection layer 10 and the catalyst layer 11. The sensor element 20 may have a bulk structure in which each layer is relatively thick, and the heater layer 6 may also serve as the electrode layer. Alternatively, as the support structure, a so-called bridge structure can be adopted.

The gas detection layer 10 is formed between the pair of electrode layers 9 on the insulating layer 7. The gas detection layer 10 is a semiconductor layer containing a metal oxide as a main component. In the present embodiment, a mixture containing tin oxide ($snO_2$) as a main component is used as the gas detection layer 10. The electric resistance value of the gas detection layer 10 changes due to contact with the detection target gas. The gas detection layer 10 may be a thin film having a thickness of about 0.2 to 1.6 μm, or a film (thick film) having a thickness more than 1.6 μm.

The catalyst layer 11 is formed on the gas detection layer 10 so as to cover the gas detection layer 10. The catalyst layer 11 is configured by supporting a catalyst metal on a support containing a metal oxide as a main component. The catalyst layer 11 is formed by bonding the metal oxide supporting the catalyst metal via a binder.

As the catalyst metal, a metal that serves as a catalyst capable of oxidizing and removing interfering gases (a reducing gas such as alcohol and hydrogen and other gases) that may cause false detection when detecting the detection target gas is used. Palladium, platinum, and iridium (Jr) can be used as the catalyst metal, but in the present embodiment, at least one of palladium, platinum, and iridium is contained.

In the related art, alumina has been mainly used as a support for supporting a catalyst metal. In the present embodiment, zirconium oxide is used as a material that is less likely to generate hydroxyl groups on the surface than alumina and can suppress the adsorption and accumulation of moisture in the air onto the catalyst layer 11.

As the binder for bonding the support, fine powder of metal oxide, for example, zirconium oxide, fine silica powder, silica sol, or magnesia can be used. If the binder is used in a small amount, it is possible to use fine alumina powder or alumina sol in a range in which the function of the catalyst layer 11 is not impaired.

The catalyst layer 11 is formed by printing a printing paste prepared by mixing zirconium oxide powder (a particle size of about 1 to 10 μm) supporting the metal oxide catalyst, the binder, and an organic solvent by screen printing, drying the resultant at room temperature, and thereafter baking the resultant at 500° C. for one hour. The size of the catalyst layer 11 is sufficient to cover the gas detection layer 10. The thickness thereof is reduced by the screen printing as described above. The specific surface area of the zirconium oxide sintered body thus formed was about 30 $m^2/g$.

As the catalyst metal, the metal oxide as the support, and the binder described above, one kind may be used alone, or two or more kinds may be used in combination.

The amount of the catalyst metal contained in the catalyst layer 11 is preferably set to 0.3 to 9 mass % with respect to the total mass of the catalyst metal and the support. In a case where two or more kinds of metals are used as the catalyst metal, the total mass of the catalyst metal is suitably set to 0.3 to 9 mass % with respect to the total mass of the catalyst metal and the support.

In a case of detecting only methane, the mass of platinum is suitably set to 0.3 mass % or more and 6 mass % or less.

(Heating Control Unit)

The gas detection device 100 for detecting methane will be described as an example. As described above, the heating drive signals for the detection are shown in FIGS. 4(a) and 4(b).

The heating control unit 12 is configured to perform an energization operation in which the heater layer 6 is energized (the timing at which the energization operation is performed is referred to as a gas detection step Ts in the present invention) and a non-energization operation in which the heater layer 6 is not energized (the timing at which the non-energization operation is performed is referred to as a heating suspension step Tr in the present invention). The energization operation (gas detection step Ts) is repeated in a gas detection cycle Rt. That is, pulse heating is repeated in the gas detection cycle Rt.

Furthermore, the heating control unit 12 is configured to fluctuate the temperature of the heater layer 6, and is configured to be able to heat the temperature of the heater layer 6 to any set temperature.

Specifically, the heating control unit 12 is supplied with power from the battery 15, and energizes the heater layer 6 of the sensor element 20 to heat the sensor element 20. The heating temperature, that is, the reaching temperature of the gas detection layer 10 and the catalyst layer 11, is controlled by, for example, changing a voltage applied to the heater layer 6.

(Gas Detection Unit) The gas detection unit 13 measures a change in the characteristics of the gas detection layer 10 at an appropriate timing in the gas detection step Ts to detect the detection target gas. In the present embodiment, the gas detection unit 13 measures the resistance value of the gas detection layer 10 by measuring the electric resistance value (an example of the characteristics) between the pair of electrode layers 9 to detect the concentration of the detection target gas from the change.

(Detection of Detection Target Gas)

A case where a flammable gas (detection target gas) such as methane or propane is detected by the gas detection device 100 configured as described above will be described.

The heater layer 6 is energized by the heating control unit 12 to heat the gas detection layer 10 and the catalyst layer 11 to 300° C. to 500° C. for methane detection for 0.05 seconds to 0.5 seconds. During this period (specifically, immediately before the stop of the energization indicated by the black circles in FIGS. 4(a) and 4(b)), the gas detection unit 13 measures the resistance value of the gas detection layer 10, and detects the concentration of a flammable gas such as methane or propane from the value.

Thereafter, the energization of the heater layer 6 is stopped. Therefore, the gas detection step Ts described as above is a high temperature heating step.

During this period, in the catalyst layer 11 which has reached a high temperature, a reducing gas such as carbon monoxide and hydrogen and other miscellaneous gases are burned by the combustion catalytic action of the catalyst metal. Then, the inactive flammable gas such as methane and propane penetrates and diffuses through the catalyst layer 11, reaches the gas detection layer 10, reacts with the metal oxide (tin oxide) of the gas detection layer 10, and changes the resistance value.

As described above, the gas detection device 100 detects the flammable gas.

The gas detection step Ts is repeated in a gas detection cycle Rt of 20 to 60 seconds, but after the gas detection step Ts, the energization is stopped (heating suspension step Tr) as shown above.

[High Humidity Exposure Experiment]

In order to investigate the effect of the kind of support material on a change in sensor sensitivity over time, samples in which only the kind of support was changed were produced, and the change in sensor sensitivity (methane sensitivity) over time was measured.

Measurement targets are the following three samples.

(High Temperature Exposure Experiment Example 1)

A sample in which 5 mass % of platinum (Pt) and 2 mass % of iridium (Jr) were supported on zirconium oxide ($ZrO_2$) as a support.

(High Temperature Exposure Experiment Example 2) A sample in which 5 mass % of platinum (Pt) and 2 mass % of iridium (Jr) were supported on titanium oxide ($TiO_2$) as a support.

(High Temperature Exposure Experiment Example 3) A sample in which 5 mass % of platinum (Pt) and 2 mass % of iridium (Jr) were supported on alumina ($Al_2O_3$) as a support.

Figure 2:
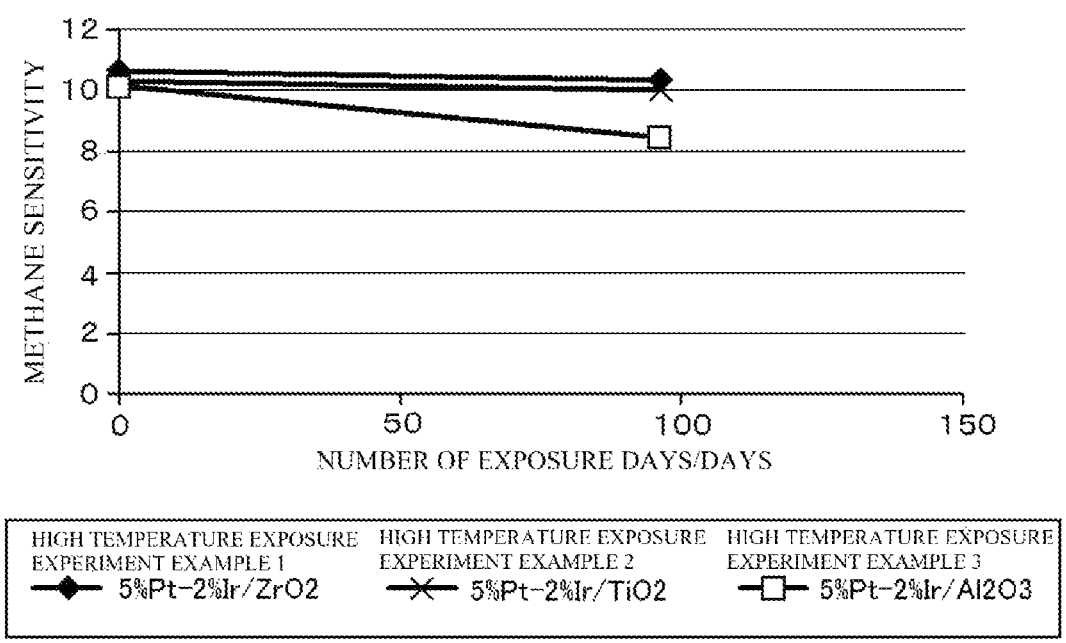
FIG. 2 is a graph showing changes over time in methane sensitivity in high humidity exposure experiments.

FIG. 2 shows a change in the methane sensitivity of the samples subjected to a 50° C. 60% RH exposure test (RCh4/Rair obtained by dividing the resistance value RCh4 in 3000 ppm methane gas when heated at 400° C. by the resistance value Rair in the air when heated at 400° C.) over time. The methane sensitivity was measured in clean air at 20° C. and 65% RH.

The gas detection is performed by repeating the pulse heating described as above in the gas detection cycle Rt (the same applies to a methane sensitivity experiment described later).

As shown in FIG. 2, in High Humidity Exposure Experiment Examples 1 and 2 in which the support was zirconium oxide or titanium oxide, the methane sensitivity had not changed over time. Contrary to this, in High Humidity Exposure Experiment Example 3 (the support was alumina), the methane sensitivity had decreased over time.

The inventors presume that this factor is due to the following. The interaction with water in the catalyst layer 11 consists of the following three steps.

(1) In the short term, OH groups are adsorbed and chemisorbed water increases.

(2) Water molecules (physisorbed water) that cannot be completely blown off during heating accumulate.

(3) Adsorbed water reacts with the bulk (support) to form hydrate.

In a case where the heating suspension step is not included, the interaction proceeds in the steps (1) to (3), and in a case where the heating suspension step is included, the interaction proceeds in the steps (2) to (3). Therefore, in a case where $SiO_2$ and $Al_2O_3$ having a strong interaction with water are used as the support, (1) is likely to occur in a high humidity in the case where the heating suspension step is not included. In the case where the heating suspension step is included as in the target of the present embodiment, (2) is likely to occur in a high humidity, and the intersection proceeds to (3) over time, thereby changing the sensitivity of the detection target gas.

In this regard, in a case where zirconium oxide or titanium oxide, which has almost no interaction with water, is used as the support, (1) is unlikely to occur even in a high humidity in the case where the heating suspension step is not included, and (2) is less likely to occur even in a high humidity in the case where the heating suspension step is included. Therefore, hydrate is not formed over time and the sensitivity does not fluctuate. Moreover, the gas sensitivity does not depend on the humidity.

[Methane Sensitivity Experiment]

In order to compare the methane sensitivity due to the difference in the kind of support and the kind and amount of the catalyst metal, 19 samples in which the kind and amount of the catalyst metal were mainly changed were produced, and the methane sensitivity under a normal environment was measured.

The methane sensitivity is the same as described above in the [High Humidity Exposure Experiment] except for the environmental conditions. That is, the methane sensitivity is $RCh_4/Rair$ obtained by dividing the resistance value $RCh_4$ in 3000 ppm methane gas when heated at 400° C. by the resistance value $Rair$ in the air when heated at 400° C.

High Temperature Exposure Experiment Examples 1 and 2 used above in the high humidity exposure experiment are Sample 16 and Sample 18.

Each sample to be measured is summarized below.

1. Kinds of supports

Samples 1 to 17: Zirconium oxide

18: Titanium oxide

19: Alumina

2. Catalyst metal

The catalyst metals to be examined were palladium (Pd), iridium (Jr), and platinum (Pt).

Tables 1, 2, 3, and 4 shown below show the amount (mass %) of the catalyst metal supported in Samples 1 to 19. Columns with blanks indicate that no catalyst metal is supported.

TABLE 1

| | Sample No. | | | | | |
|---|---|---|---|---|---|---|
| | 1 | 2 | 3 | 4 | 5 | 6 |
| Pd | 1 | | 3 | 3 | 0.5 | |
| Ir | 1 | 3 | | 2 | | 0.5 |
| Pt | 1 | 2 | 2 | | 0.5 | 0.5 |

TABLE 2

| | Sample No. | | | | | |
|---|---|---|---|---|---|---|
| | 7 | 8 | 9 | 10 | 11 | 12 |
| Pd | | | | 1 | | 1 |
| Ir | 1 | | 0.5 | | 1 | 1 |
| Pt | 0.5 | 1 | 1 | 1 | 1 | |

TABLE 3

| | Sample No. | | | | | |
|---|---|---|---|---|---|---|
| | 13 | 14 | 15 | 16 | 17 | 18 |
| Pd | | 2 | | | 7 | |
| Ir | | | 2 | 2 | | 2 |
| Pt | 3 | 2 | 2 | 5 | | 5 |

TABLE 4

| | Sample No. |
|---|---|
| | 19 |
| Pd | 7 |
| Ir | |
| Pt | |

Furthermore, FIG. 3 shows the methane sensitivity of each sample.

Sample numbers are shown in the upper part of the figure, and the kinds and concentrations (mass %) of the metal oxide catalysts are shown in the lower part of the figure.

As a result, the methane sensitivity of Sample 17 in which only the support was changed to zirconium oxide was increased with respect to Sample 19 (alumina support and 7 mass % palladium) corresponding to the related art.

In both the samples, Sample 17 was a preferable result in which the sensitivity did not change even in the high humidity exposure experiment conducted separately.

Furthermore, all the samples (1 to 17) using zirconium oxide as a support for comparison had higher sensitivity to methane than Sample 19.

Sample 18 using titanium oxide as a support for comparison had higher sensitivity to methane than Sample 19.

Compared to High Temperature Exposure Experiment Example 3 (alumina support, 5 mass % platinum, and 2 mass % iridium) described above, Samples 1 to 18 showed methane sensitivity equal to or higher than that of High Temperature Exposure Experiment Example 3.

Among the samples to be examined, the samples (8 and 13) in which zirconium oxide was used as a support and the catalyst metal was only platinum showed particularly high methane sensitivity.

As a result, it was determined that a combination using only platinum as the catalyst metal with zirconium oxide as the support is particularly preferable as a gas sensor.

When Sample 8 and Sample 13 are compared to each other, Sample 13 having a higher platinum concentration has a higher methane sensitivity, so that the higher the platinum concentration, the higher the methane sensitivity. On the other hand, when Sample 15 and Sample 16 are compared to each other, the higher the platinum concentration is, the lower the methane sensitivity is for the same iridium concentration. From the above, regarding the platinum concentration, the higher the concentration is, the higher the methane sensitivity becomes. However, when the concentration exceeds a certain concentration, the methane sensitivity becomes lower. From this, it can be seen that an appropriate concentration range for obtaining a high methane sensitivity is present. It is considered that the reason why the methane sensitivity decreases beyond a certain concentration is that the oxidative activity of platinum increases and even methane is burned and oxidized in the catalyst layer. From the above, it is considered that the concentration of platinum is 0.3 mass % or more and 9 mass % or less, it is desirable that the concentration of platinum is suitably 0.3 mass % or more and 6 mass % or less.

[Another Embodiment]

(1) In the above experiment, the significance of the present invention has been described in the experiment example relating to methane as an example of the flammable gas. However, as described as above, a hydrocarbon gas having a small number of carbon atoms such as propane can be detected by the gas detection device according to the present invention.

(2) In the above experiment, the example in which the support supporting the catalyst metal is zirconium oxide and titanium oxide has been described. However, as described earlier in paragraph [0016], since a transition metal oxide has a weak interaction with water, the transition metal oxide can be adopted as the support for supporting the catalyst metal.

(3) In a case where the support is formed of a transition metal oxide, in the above experiment, an example in which the support is formed of only zirconium oxide or titanium oxide has been described. However, the support of the catalyst portion may be configured with the transition metal oxide as a main component. Here, the main component means 50 mass % or more (in a case of a plurality of transition metal oxides, the total mass thereof is 50 mass % or more).

Furthermore, in the present invention, the catalyst metal suitably has platinum as the main component and has a catalyst concentration of 0.3 to 9 mass % with respect to the total mass with the support.

Here, having platinum as the main component means that platinum is supported within the above range and in a case where other metal oxide catalysts (one or more selected from palladium and iridium) are contained, the amount thereof is smaller than the amount of platinum.

(4) In the above description, the case where methane is detected by the heating drive signals shown in FIGS. 4(a) and 4(b) has been mainly described. However, as shown in FIG. 4(c), methane detection may be followed by carbon monoxide detection, or methane and carbon monoxide may be alternately detected. In detecting carbon monoxide, the gas detection layer 10 and the catalyst layer 11 are heated to 50° C. to 250° C. During this period (specifically, immediately before the stop of the energization indicated by the black circle in FIG. 4(c)), the gas detection unit 13 may measure the resistance value of the gas detection layer 10 and detect the concentration of carbon monoxide from the value.

In FIG. 4(c), carbon monoxide is continuously detected subsequent to the methane detection, but a heating suspension step of stopping the energization of the heater portion may be interposed between the two detections.

(5) In the above-described embodiment, the case where the energization of the heater portion in the gas detection step Ts is pulse energization in which the energization time is 0.05 seconds to 0.5 seconds, and the pulse energization is repeated in a gas detection cycle Rt of 20 seconds to 60 seconds with the heating suspension step Tr has been described.

This energization form is a form in which so-called pulse heating is repeated in a predetermined gas detection cycle Rt, and as described above, is an example of an energization form that is basically used in normal times.

Therefore, while this basic energization form is performed, for example, in a case where there is a possibility that methane may be detected, the gas detection cycle, which is the cycle of pulse energization (pulse heating), can be set to any short cycle, for example, a cycle of 5 seconds to 10 seconds.

On the other hand, regarding the relationship between the heating time in the gas detection step and the heating stop time in the heating suspension step, as described above, it is preferable that the former is shorter than the latter in terms of power saving.

(6) In the above-described embodiment, an example in which the energization of the heater portion in the gas detection step Ts is pulse energization in which the pulse energization time is 0.05 seconds to 0.5 seconds has been described. However, in a case where the gas detection cycle Rt is 20 seconds to 60 seconds, the energization time may be set to 5 seconds or shorter.

(7) Furthermore, in the embodiment described as above, an example in which the heating suspension step Tr for suspending the heating is performed after the gas detection step Ts has been described.

However, from the intent of the present invention, it is preferable in terms of moisture resistance that the gas detection portion and the catalyst portion are heated by energizing the heater portion during a time zone corresponding to the heating suspension step Tr.

Figure 5A:
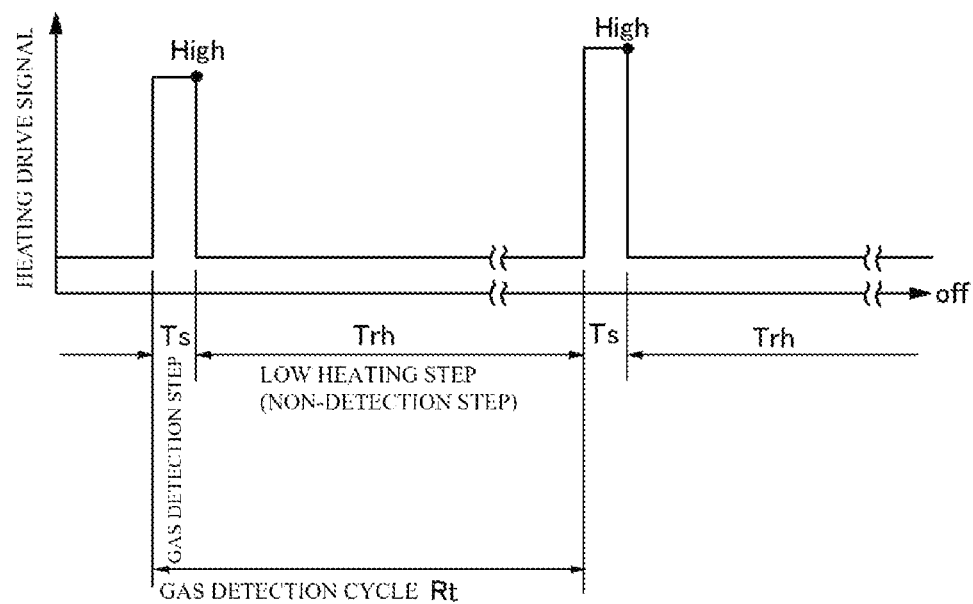
FIGS. 5(a)-5(c) are explanatory diagrams showing another embodiment of heating drive.
Figure 5B:
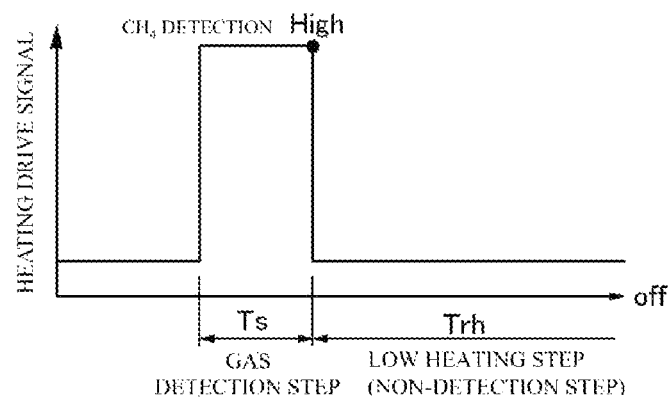
Figure 5C:
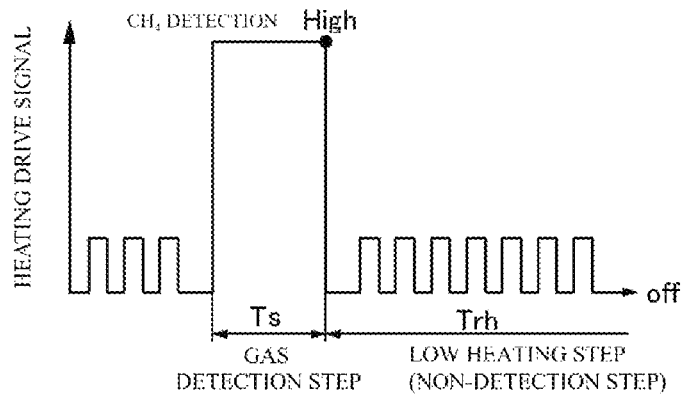

Therefore, during the gas detection step of energizing the heater portion to heat the gas detection portion and the catalyst portion and detecting the detection target gas, a low heating step Trh of heating the gas detection portion and the catalyst portion to a temperature (for example, in a case of performing only the methane detection, a temperature lower than 100° C. and higher than room temperature, and in a case with carbon monoxide detection, a temperature lower than a carbon monoxide detection temperature, lower than 100° C., and higher than room temperature (in a case where the carbon monoxide detection is performed at 100° C., a temperature of about 50° C.)) lower than the temperatures reached by the gas detection portion and the catalyst portion in the gas detection step may be performed. FIGS. 5(a)-5(c) show an example of performing such a low heating step. FIG. 5(a) is an explanatory diagram corresponding to FIG. 4(a), in which the low heating step Trh is performed subsequent to the gas detection step Ts. In the low heating step Trh, a certain degree of heating is performed by performing a certain degree of energization. In the example shown in the figure, the gas detection cycle Rt is established by combining the gas detection step Ts with the low heating step Trh subsequent thereto. Both FIGS. 5(b) and 5(c) are examples in which methane detection is performed, in which FIG. 5(b) is an example of setting the low heating to a constant heating state shown in FIG. 5(a). In FIG. 5(c), the low heating is performed by heating suspension (stop of energization) and heating (energization).

That is, in a configuration in which a non-detection step in which gas detection is not performed is performed after the gas detection step Ts in which gas detection is performed, the non-detection step can be set to the heating suspension step Tr or the low heating step Trh. However, in the non-detection step, heating suspension (stop of energization) and heating (energization) may be combined in any form, and the temperature of the gas detection portion and the catalyst portion in the non-detection step may be set to a state lower than the temperature of both the portions in the gas detection step. In this case, when the temperature of both the portions is maintained at a temperature that is not easily affected by water, the generation of hydrate can be inhibited. The combination of heating suspension (stop of energization) and heating (energization) here naturally includes one or more of selection of the timing of the combination and selection of the magnitude of the amount of energization. The temperature may change over time.

Furthermore, the temperature control in the non-detection step may be performed by any means, for example, means different from the energization of the heater portion.

(8) However, in the above-described embodiment, the structure of the gas sensor (gas detection element 20) forming a part of the gas detection device 100 is of a so-called substrate type shown in FIG. 1, but other structures are also possible. For example, a structure in which the heater layer 6 also serves as the electrode layer 9 is possible without providing the insulating layer 7 that covers the heater layer 6.

Figure 6:
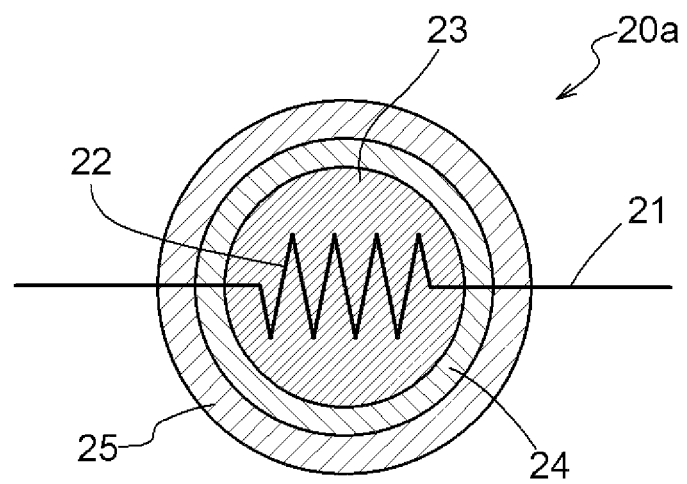
FIG. 6 is a diagram showing another embodiment of a gas sensor.

Furthermore, for example, as illustrated in FIG. 6, as a gas sensor 20a, a structure in which a gas detection portion 23 made of an oxide semiconductor is formed around a coil 22 of an electrode wire 21 which serves as both an electrode and a heater portion, and catalyst layers (catalyst portions) 24 and 25 are formed around the gas detection portion 23 is also possible. Here, the catalyst layers have two layers, but may also be a single layer. In the case of the two layers, the ratio of the catalyst metal between the layers can be changed. In this case, having platinum as the main component means that the amount of platinum in at least one layer is within the above-mentioned amount range and is larger than the amount of other catalyst metals.

Figure 7:
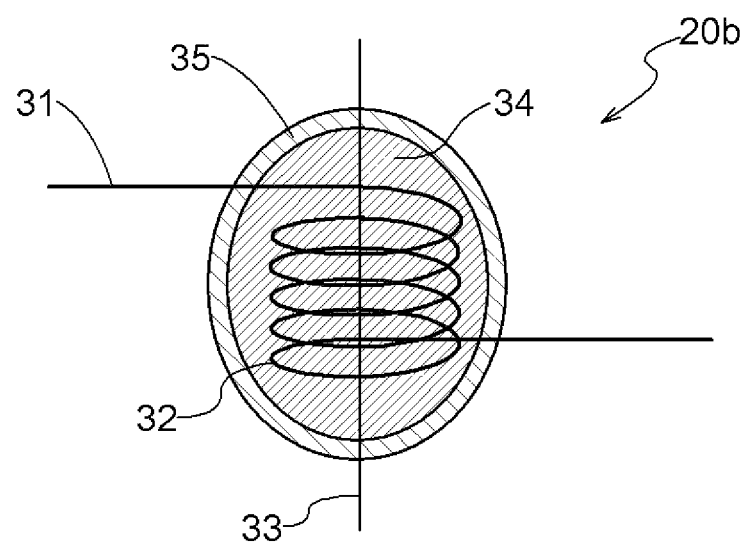
FIG. 7 is a diagram showing another embodiment of the gas sensor.

Furthermore, as shown in FIG. 7, as a gas sensor 20b, a structure in which at the center of a coil 32 of an electrode wire 31 which serves as both an electrode and a heater portion, another electrode 33 is disposed, a gas detection portion 34 made of an oxide semiconductor is disposed around the coil 32, and a catalyst layer 35 is formed around the gas detection portion 34 is also possible.

The gas detection device 100 may be a gas detection device that includes a gas sensor including a heater portion, a gas detection portion whose characteristics change due to contact with a detection target gas, and a catalyst portion covering at least a part of the gas detection portion, energizes the heater portion to heat the gas detection portion and the catalyst portion, and detects the detection target gas, and is not limited to the embodiments described as above.

(9) Furthermore, the catalyst portion in which the catalyst metal containing platinum as the main component is supported on the support containing the transition metal oxide as the main component may be provided to cover at least a part of the gas detection portion. This is because it is considered possible to selectively burn the interfering gas by providing such a catalyst portion.

The invention claimed is:

1. A gas detection device comprising:
a gas sensor comprising a heater portion, a gas detection portion whose characteristics change due to contact with a detection target gas, and a catalyst portion provided to cover at least a part of the gas detection portion,
wherein the gas detection device energizes the heater portion to heat the gas detection portion and the catalyst portion and detects the detection target gas, and the catalyst portion is configured to support a catalyst metal containing platinum as a main component on a support containing a transition metal oxide as a main component.

2. The gas detection device according to claim 1, wherein the transition metal oxide is one or both of zirconium oxide and titanium oxide.

3. The gas detection device according to claim 1, wherein the catalyst portion is configured to support 0.3 mass % or more and 9 mass % or less of platinum as the catalyst metal on the support.

4. The gas detection device according to claim 1, wherein one or both of palladium and iridium are contained as the catalyst metal in addition to platinum as the main component.

5. The gas detection device according to claim 1, wherein the detection target gas is detected by repeating a gas detection step of energizing the heater portion to heat the gas detection portion and the catalyst portion and detecting the detection target gas, and a non-detection step of setting temperatures of the gas detection portion and the catalyst portion to be in a state lower than temperatures of the gas detection portion and the catalyst portion in the gas detection step.

6. The gas detection device according to claim 1, wherein the detection target gas is detected by repeating a gas detection step of energizing the heater portion to heat the gas detection portion and the catalyst portion and detecting the detection target gas, and a low heating step of performing energization to set temperatures of the gas detection portion and the catalyst portion to be temperatures lower than temperatures of the gas detection portion and the catalyst portion in the gas detection step.

7. The gas detection device according to claim 1, wherein the detection target gas is detected by repeating a gas detection step of energizing the heater portion to heat the gas detection portion and the catalyst portion and detecting the detection target gas, and a heating suspension step of stopping the energization of the heater portion.

8. The gas detection device according to claim 7, wherein a heating time in the gas detection step is shorter than a heating stop time in the heating suspension step.

9. The gas detection device according to claim 7, wherein at least the heating in the gas detection step is pulse heating having a heating time of 0.05 seconds to 0.5 seconds, and
at least a basic heating form of repeating the pulse heating in a gas detection cycle of 20 seconds to 60 seconds with the heating suspension step is performed.

10. The gas detection device according to claim 1, wherein
a high temperature heating step of heating the gas detection portion and the catalyst portion to a temperature for detecting methane is performed when detecting the detection target gas.

* * * * *